US00PP32517P2

(12) United States Plant Patent
Goldstein et al.

(10) Patent No.: US PP32,517 P2
(45) Date of Patent: Nov. 24, 2020

(54) GARLIC PLANT NAMED 'NEVADA 19'

(50) Latin Name: ***Allium sativum* L.**
Varietal Denomination: NEVADA 19

(71) Applicants: State of Israel, Ministry of Agriculture & Rural Development, Agricultural Research Organization, Rishon Lezion (IL); Yissum Research Development Company of the Hebrew University of Jerusalem LTD., Jerusalem (IL)

(72) Inventors: Rina Kamenetsky Goldstein, Rehovot (IL); Einat Shemesh-Mayer, Kiryat Ono (IL); Haim D. Rabinowitch, Kiryat Ono (IL); Tomer Efraim Ben Michael, Rehovot (IL); Chen Gershberg, Rehovot (IL); Izhak Forer, Nes Ziona (IL)

(73) Assignees: State of Israel, Ministry of Agriculture & Rural Development, Agricultural Research Organization, Rishon Lezion (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 16/501,537

(22) Filed: Apr. 29, 2019

(51) Int. Cl.
*A01H 5/02* (2018.01)
*A01H 6/04* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
*Assistant Examiner* — Karen M Redden
(74) *Attorney, Agent, or Firm* — Foley & Lardner LLP

(57) ABSTRACT

A new and distinct variety of garlic plant, *Allium sativum* L., named 'NEVADA 19', particularly characterized by suitability for growing under climatic conditions such as prevailing in Nevada and California, regular bulb structure, good storage quality, white cover scale color, good clove peeling ability; and mid-season bulb harvest time.

4 Drawing Sheets

Botanical name of the genus and species of the plant claimed: *Allium sativum* L.

Variety denomination: 'NEVADA 19'.

BACKGROUND OF THE INVENTION

The present invention relates to a new and distinct variety of garlic plant, botanically known as *Allium sativum* of the Amaryllidaceae family, and hereinafter referred to by the variety denomination 'NEVADA 19'. The breeder's reference is 'V-19-G (line GH17-F1-19-c-B3)'.

The new *Allium sativum* variety is a product of a planned breeding program conducted by the inventors, Rina Kamenetsky Goldstein, Einat Shemesh-Mayer, Haim D. Rabinowitch, Tomer Efraim Ben Michael, Chen Gershberg, and Izhak Forer, in Bet Dagan, Israel, following by the field vegetative propagation in Yerington, Nev., U.S.A. The objective of the breeding program was to develop a new *Allium sativum* variety suitable for growing under climatic conditions such as prevailing in Nevada and California, regular bulb structure, good storage quality, white cover scale color, good clove peeling ability and mid-season bulb harvest time.

The new *Allium sativum* variety originated from a cross made by the inventors in 2012 in Bet Dagan, Coastal Plain, Israel. The female or seed parent is the *Allium sativum* designated GR11-F1-998-b-B4 (unpatented). This plant is characterized by flowering ability, male sterility and relatively small bulbs. The male or pollen parent is the *Allium sativum* designated GR11-F1-999-b-B4 (unpatented). Both parents, female and male, resulted from previous crosses conducted in 2004 in Bet Dagan, Coastal Plain, Israel. In 2004, following the restoration of garlic fertility, about 10,000 seeds were obtained by uncontrolled outcrossing in 2004, and further selection for flowering ability was performed. In 2012, the cross between selected female and male parents was made in Israel. In 2012-2013, the seedling population, resulting from this cross, produced mini-bulbs (so-called sets), in Bet Dagan, Israel. In 2014, about 1000 plants from these set populations were grown in Gilroy, Calif. Subsequently, 12 single excelling plants were observed and selected and each was propagated in vitro for fast multiplication. Further selection resulted finally in the outstanding new variety 'NEVADA 19'.

Asexual (vegetative) propagation of the new *Allium sativum* variety by micro propagation was first performed in 2015 in Gilroy, Calif., U.S.A, using tissue culture. Plant explants were grown on sterile agar medium with addition of minerals, microelements, sugar and plant hormones. The obtained plantlets were hardened in a greenhouse and then in September 2015 transplanted to the propagation field in Nevada. These transplants produced plants and bulbs which demonstrated that the combination of characteristics as herein disclosed for the new variety are firmly fixed and retained through successive generations of asexual propagation. The new variety propagates true-to-type.

BRIEF DESCRIPTION OF THE INVENTION

The following traits have been repeatedly observed and are determined to be characteristics of 'NEVADA 19' which in combination distinguish this garlic plant as a new, unique and distinct variety:

1. suitability for growing under conditions such as prevailing in California and Nevada, USA;
2. regular bulb structure;
3. white cover scale color;
4. good clove peeling ability; and
5. mid-season bulb harvest time.

In comparison to the parental varieties, 'GR11-F1-998-b-B4' (unpatented) and 'GR11-F1-999-b-B4' (unpatented), 'NEVADA 19' differs primarily in the traits listed in Table 1.

TABLE 1

Comparison with parent varieties.

| Trait | New Variety 'NEVADA 19' | Female Parent 'GR11-F1-998-b-B4' (unpatented) | Male Parent 'GR11-F1-999-b-B4' (unpatented) |
|---|---|---|---|
| pollen production | none | none | high |
| pollen germination | N/A | N/A | yes |
| bulb size | large | medium | relatively large |
| bulb shape | regular | regular | irregular |
| skin color | white | grey-violet | white |
| time of bulbing | medium | late | medium |

Of the local commercial varieties known to the present inventors, the most similar in comparison to the new *Allium sativum* 'NEVADA 19' are the varieties 'California Early' and 'California Late' (unpatented), which differ from the new garlic 'NEVADA 19' in the characteristics described in Table 2:

TABLE 2

Comparison with well known commercial varieties.

| Characteristic | New Variety 'NEVADA 19' | Comparison Variety 'California Early' (unpatented) | Comparison Variety 'California Late' (unpatented) |
|---|---|---|---|
| harvest time | mid-season (June-July) | early (June) | late (July) |
| bulb type | hardneck | softneck | hardneck |
| bulb size | large | large | large |
| bulb shape | regular | irregular | irregular |
| clove size | large | varies | medium to large |
| skin color | white | white | white |

BRIEF DESCRIPTION OF THE PHOTOGRAPHS

The accompanying photographs illustrate the overall appearance of the new *Allium sativum* variety 'NEVADA 19' showing the colors as true as is reasonably possible with colored reproductions of this type. Colors in the photographs may differ slightly from the color values cited in the detailed morphological description, which accurately describe the color of 'NEVADA 19'.

Figure 1:
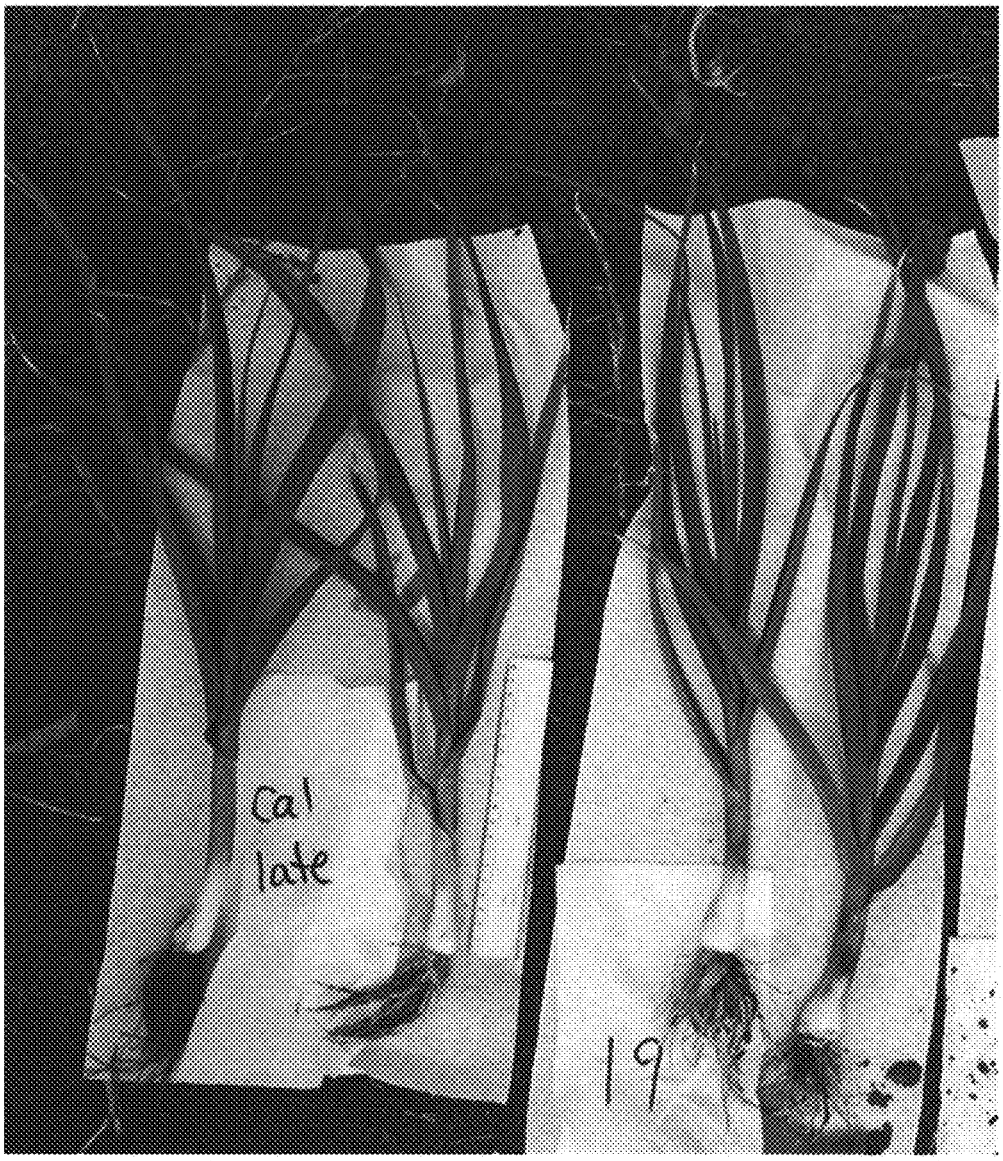
FIG. 1 shows typical plants of 'NEVADA 19' in comparison with typical plants of 'California Late'
Figure 2:
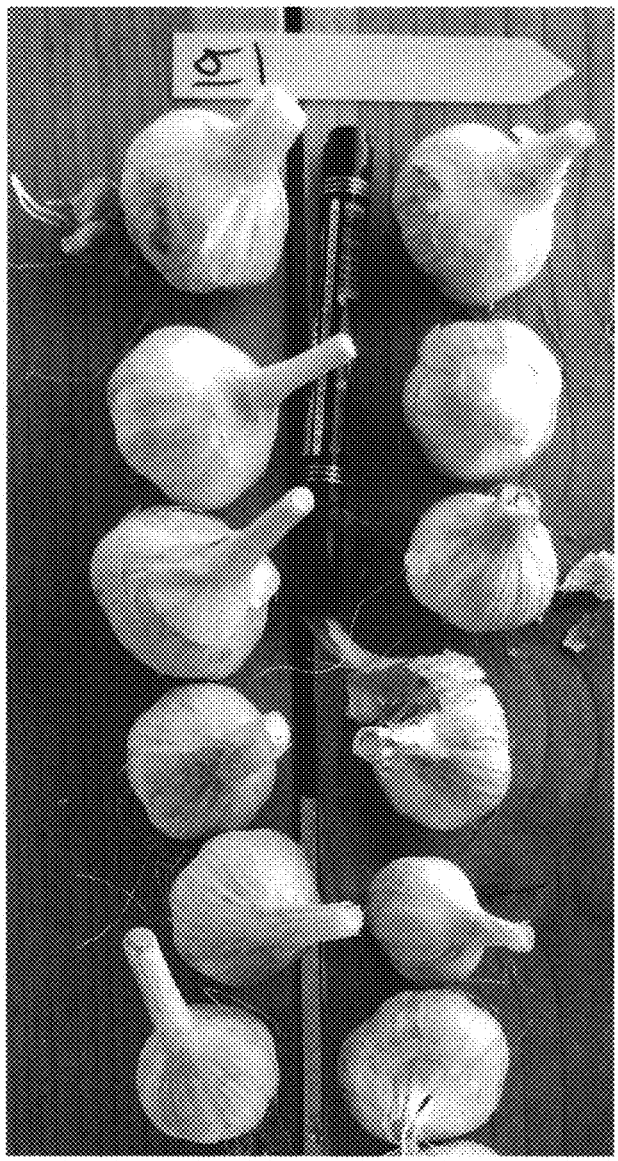
FIG. 2 shows typical bulbs of 'NEVADA 19'
Figure 3:
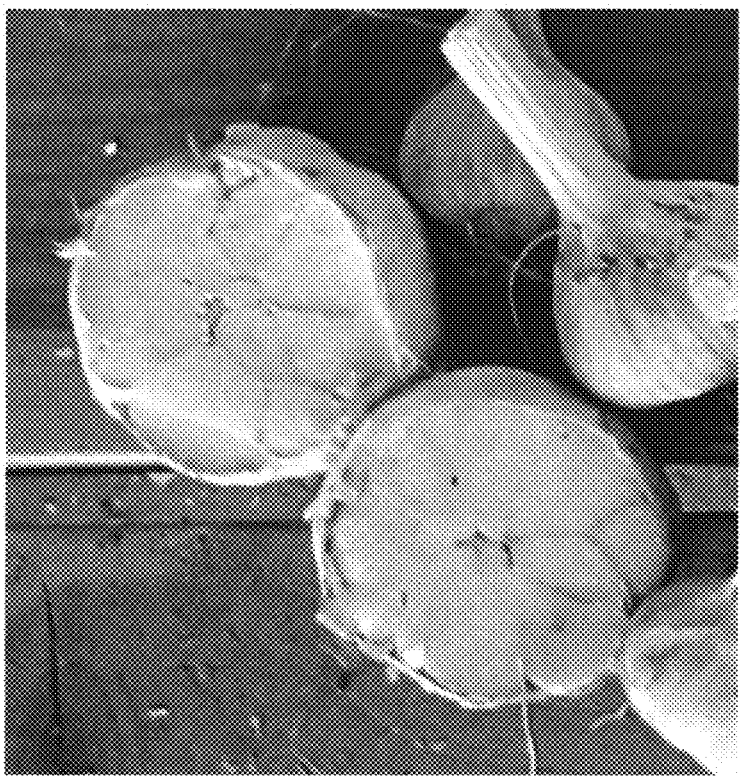
FIG. 3 shows a cross-section view of a typical bulb of 'NEVADA 19'
Figure 4:
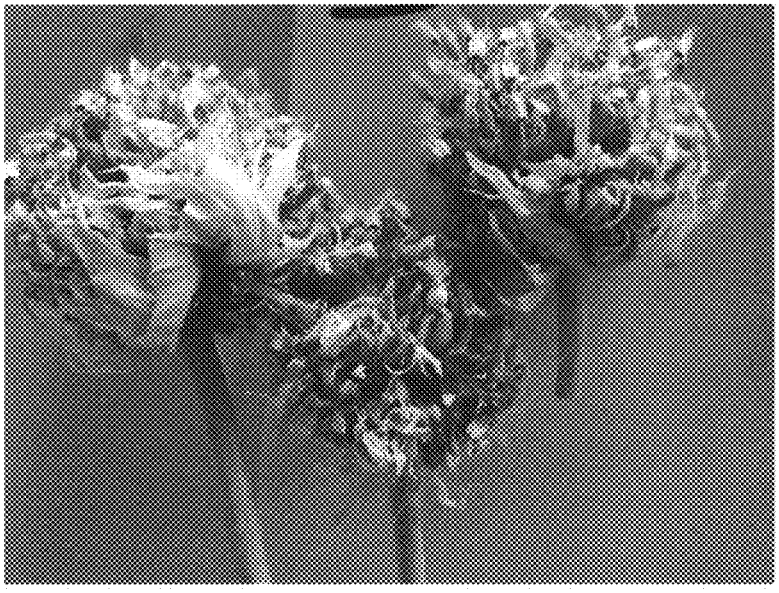
FIG. 4 shows a typical inflorescence of 'NEVADA 19'

Color designations stated for the new variety may vary, depending upon variations in environmental factors, including weather (temperature, humidity and light intensity), day length, soil type, location and cultural conditions. 'NEVADA 19' has not been observed under all possible environmental conditions.

DETAILED BOTANICAL DESCRIPTION

The new *Allium sativum* 'NEVADA 19' has not been observed under all possible environmental conditions. The phenotype of the new variety may vary with variations in environment such as temperature, light intensity, day length, soil or storage conditions without any change in the genotype of the garlic plant.

The aforementioned photographs, together with the following observations, measurements and values describe plants of 'NEVADA 19' as grown in the farm in Gilroy, Calif., U.S.A under conditions which closely approximate those generally used in commercial practice.

Unless otherwise stated, the detailed morphological description includes observations, measurements and values taken in 2017 and 2018 of plants grown in the farm in Gilroy, Calif., U.S.A. Quantified measurements are expressed as an average or a range of measurements taken from a number of plants of 'NEVADA 19'. The measurements of any individual plant, or any group of plants, of the new variety may vary from the stated average or range.

Color references are made to The Royal Horticultural Society Colour Chart (R.H.S.), (1986 edition), except where general colors of ordinary significance are used. Color values were taken under daylight conditions in full sunlight in Gilroy, Calif., U.S.A.

All of the plants of 'NEVADA 19', insofar as they have been observed, have been consistent in all the characteristics described below.

Classification:

*Botanical.*—*Allium sativum* L.

Parentage:

*Female or seed parent.*—*Allium sativum* 'GR11-F1-998-b-B4' (unpatented).

*Male or pollen parent.*—*Allium sativum* 'GR11-F1-999-b-B4' (unpatented).

Propagation:

*Propagation area for planting material.*—Nevada, USA.

*Planting time.*—September in Nevada, USA.

*Harvesting time.*—July-August in both California and Yerington, Nev., USA. Production cycle includes planting in September 10, water cut on June 15 and harvest on August 1.

*Root development prior to cold period.*—Yes.

*Local soil.*—Light clay.

Growing conditions:

*Light intensities.*—Full sunlight.

*Temperature.*—Average temperature: 53.45° F.

*Annual low temperature.*—38° F.

*Annual high temperature.*—68.9° F.

*Average annual precipitation.*—4.83 inches.

*Fertilization.*—A balanced of 10:10:10 (N:P:K) fertilizer with microelements.

*Growth regulators.*—None used.

*Plant.*—Total height (including inflorescence): about 70 cm. Arrangement of leaves: basal. Height of foliage: 50-70 cm. Density of foliage: medium dense. Growth habit: erect.

*Young leaf*.—Color of upper surface: dark green RHS 135 B. Color of lower surface: dark green RHS 135 B.

*Mature leaf*.—Color of upper surface: dark green RHS 136 B. Color of lower surface: dark green RHS 136 B. Waxiness: medium waxy. Length (longest leaf): long, about 30 cm. Width (longest leaf): medium, about 1.5 cm. Longitudinal axis: slightly curved at ⅓ from tip. Shape in cross section: strongly concave. Margin: entire, not undulated. Venation: parallel. Shape of apex: acute. Shape of base: obtuse. Stipules: absent.

*Pseudostem*.—Color at base: weak to medium, purple RHS 81 C. Width of the base: medium, about 2 cm.

*Flowering stem*.—Present. Curvature: present, curved stem. Length: up to 70 cm. Diameter: about 5 mm. Color: medium green RHS 138 B. Number of bulbils: 50-80.

*Flower bud*.—Length: 2-4 mm. Shape: oblong. Color: very light to light purple RHS 76 D.

*Time of opening of scape*.—Mid-May.

*Beginning of flowering*.—Early June.

*Duration of flowering*.—About one month.

*Inflorescence: type*.—Umbel.

*Umbel*.—General shape: oblong to globular. Height: 3-4 cm. Diameter: 2-4 cm. Number of flowers: 30-50.

*Pedicel*.—Length: about 1 cm. Color: medium to dark purple RHS 76 B. Thickness: about 1 mm. Surface: glabrous.

*Flower*.—Type: actinomorphic. Length: 3-4 mm. Diameter: 2-5 mm. Number of petals: six. Frangrance: none.

*Petal*.—Length: 3-4 mm. Width: about 2 mm. Shape: oblong. Texture: smooth. Margin: entire, not undulated. Color of upper surface: very light purple red RHS 69 D. Color of lower surface: very light purple red RHS 69 D.

*Stamen*.—Length: 5-7 mm. Length of filament: 4-5 mm.

*Anther*.—Length: about 2.2 mm. Width: about 1.5 mm.

*Style*.—Length: 1-1.5 cm. Color: white RHS 155 C.

*Ovary*.—Length: about 3 cm. Diameter: about 4.5 cm.

*Bulb*.—Size: medium, length of about 3 cm and diameter of about 4.5 cm. Weight: 50-60 g. Shape in longitudinal section: transverse broad elliptic. Shape in cross section: circular. Position of cloves at tip of bulb: at same level. Position of root disc: flat. Shape of base: flat. Compactness of cloves: compact. Ground color of dry external scales: white, RHS 155 B. Color of stripes on dry external scales: medium to dark purple RHS 76 B. Skin adherence of dry external scales: strongly adherent. Thickness of dry external scales: medium. Number of cloves: eight. Distribution of cloves: radial. External cloves: none.

*Clove*.—Size: length: about 1.5 cm. Width: about 2 cm. Weight: 6-10 g. Color of scale: white RHS 155 D. Intensity of color of scale: medium. Anthocyanin stripes on scale: very light to light yellowish white RHS 158 C. Color of flesh: off-white RHS 155 B. Pungency: strong.

*Seed*.—Presence: none due to flower abortion.

*Time of harvest maturity*.—Early July.

*End of dormancy of clove in bulb*.—Between mid-October and mid-November.

*Productivity of the plant* (*i.e. pounds per bushels per acre*).—5 ton per acre (12.5 ton P85 per ha).

*Storability*.—5 to 6 months.

Disease resistance: No atypical resistance has been noted.

Pest resistance: No atypical resistance has been noted.

Disease susceptibility: None observed.

Pest susceptibility: None observed.

What is claimed is:

1. A new and distinct variety of *Allium sativum* L. plant named 'NEVADA 19', as illustrated and described herein.

* * * * *